(12) United States Patent
Semerdjian

(10) Patent No.: US 6,640,588 B2
(45) Date of Patent: Nov. 4, 2003

(54) METHOD OF MAKING MICROPOROUS STRUCTURE DEFINED BY A MULTIPLICITY OF SINGULAR CHANNELS

(75) Inventor: Roy V. Semerdjian, Sacramento, CA (US)

(73) Assignee: UOP LLC, Des Plaines, IL (US)

( * ) Notice: Subject to any disclaimer, the term of this patent is extended or adjusted under 35 U.S.C. 154(b) by 159 days.

(21) Appl. No.: 10/001,372

(22) Filed: Oct. 25, 2001

(65) Prior Publication Data

US 2002/0053762 A1 May 9, 2002

Related U.S. Application Data

(62) Division of application No. 09/385,163, filed on Aug. 30, 1999, now Pat. No. 6,357,484.
(60) Provisional application No. 60/098,457, filed on Aug. 31, 1998.

(51) Int. Cl.$^7$ ............................................. C03B 37/025
(52) U.S. Cl. ............................. 65/393; 65/409; 65/411; 65/439; 65/477
(58) Field of Search .................. 65/439, 393, 409, 65/411, 477

(56) References Cited

U.S. PATENT DOCUMENTS

| | | | |
|---|---|---|---|
| 2,687,147 A | 8/1954 | Feichter | 138/44 |
| 2,825,203 A | 3/1958 | Bertin et al. | 60/35.6 |
| 3,250,469 A | 5/1966 | Colston | 235/200 |
| 3,294,504 A * | 12/1966 | Hicks | 65/393 |
| 3,380,817 A * | 4/1968 | Gardner | 65/393 |
| 3,622,291 A * | 11/1971 | Fleck et al. | 65/393 |
| 3,645,298 A | 2/1972 | Roberts et al. | 138/40 |
| 3,679,384 A * | 7/1972 | Colson | 65/439 |
| 3,805,387 A * | 4/1974 | Siegmund et al. | 30/346.53 |
| 3,838,598 A | 10/1974 | Tompkins | 73/205 L |
| 3,990,874 A * | 11/1976 | Schulman | 65/393 |
| 3,996,025 A | 12/1976 | Gulden | 48/107 |
| 4,127,398 A * | 11/1978 | Singer, Jr. | 65/393 |
| 4,293,415 A | 10/1981 | Bente, III et al. | 210/198.2 |
| 4,590,492 A * | 5/1986 | Meier | 347/242 |
| 5,028,036 A | 7/1991 | Sane et al. | 266/227 |
| 5,255,716 A | 10/1993 | Wilcox | 138/44 |
| 5,392,815 A | 2/1995 | Stuart | 138/37 |
| 5,429,653 A * | 7/1995 | Leber et al. | 65/385 |
| 5,498,324 A | 3/1996 | Yeung et al. | 204/452 |
| 5,552,042 A | 9/1996 | Le Febre et al. | 210/198.2 |
| 5,584,982 A | 12/1996 | Dovichi et al. | 204/603 |
| 5,653,777 A | 8/1997 | Semerdjian | 65/17.2 |
| 5,916,837 A | 6/1999 | Harmer et al. | 502/170 |

OTHER PUBLICATIONS

Merriam Webster's Collegiate Dictionary, 10$^{th}$ ed. p. 3.*
Article "How Many Wires Can Be Packed Into a Circular Conduit?" by Jacques Dutka, *Machinery*, Oct. 1956, pp. 245–246.

* cited by examiner

*Primary Examiner*—John Hoffmann
(74) *Attorney, Agent, or Firm*—John G. Tolomei; James C. Paschall

(57) ABSTRACT

A microporous structure can be formed from ductile material such as glass into an axially extended outer wall surrounding a plurality of singular micro-passages surrounded by the outer wall to provide an open area that extends continuously over the length of the outer wall. The diameter of the micro-passages will usually not exceed 25 μm and are more in range of from 0.5 to 5 μm. The structure is particularly useful as frits for the containment of packing in capillaries for chromatograph applications and more generally as flow restrictors. Continuous open diameters of the micro-passages have a relatively straight flow path that reduces pressure drop relative to the random arrangement of other frits while still providing the desired containment.

8 Claims, 1 Drawing Sheet

METHOD OF MAKING MICROPOROUS STRUCTURE DEFINED BY A MULTIPLICITY OF SINGULAR CHANNELS

CROSS-REFERENCE TO RELATED APPLICATION

This application is a Division of application Ser. No. 09/385,163 filed Aug. 30, 1999, now U.S. Pat. No. 6,357,484, which application claims priority from Provisional Application Serial No. 60/098,457 filed Aug. 31, 1998, the contents of which are hereby incorporated by reference in its entirety.

FIELD OF THE INVENTION

This invention relates to the making of microporous structures with micro-channels that are particularly useful as containment devices.

BACKGROUND OF THE INVENTION

In capillary electrochromatography (CEC) and related analytical methods, there are currently no repeatable techniques or materials which ensure that the medium inside the capillary does not leak. There is a need, especially in the separation sciences, for fluid-permeable containment devices to retain fluids or packings or to filter particles from flowing streams of gas or liquid Common containment devices for this purpose include fiberglass packings, screens, and bonded particles, typically referred to as frits.

There are many different methods of making frits but most techniques employ the consolidation of small particles by sintering or melting compressed particles of a known size together. In one typical method, an appropriate material is ground up into small pieces and screened for a selected size range of particles. The particles are then compressed together in a mold and heated. The objective is to apply sufficient heat to fuse the particles together but not to melt the particles. Generally, the heating cycle is moderately complex in that there is a temperature profile of several different temperatures and times that give the best results After heating, the mold is removed and the resultant maze of material is then further processed by machining to trim the edges and/or welded or glued to an appropriate substrate. Another approach uses filaments of a given diameter and length that are randomly arranged, compressed, and fused together. The materials that are common to frit manufacture are both metals and plastics The present art in this type of frit manufacture is to a) size the particles or strands, b) determine the amount of compression needed in the mold, and c) determine the temperature cycle to produce restrictive paths that have a nominal diameter of distribution. This means that the void space within these matrices have a consistent cross-sectional shape. The greater the void space relative to the total cross-sectional volume, the better the frit. The narrower the pore diameter distribution, the better the frit, and the more consistent the path length of the pores, the better the frit. The technology seems to be based more on statistics than on rigorous mechanical design since it is impossible to position millions of particles or filaments exactly in some geometrical pattern. Chaos theory appears to be the primary means of predicting performance.

Screens provide a containment device that serves as an alternate to frits but screens generally have a lower limit of performance based on the size of the wire or filament used. This lower limit is probably in the range of 25 to 125 $\mu$m and is established by the tensile strength of the filament and its ductility which is needed in the weaving process (over and under lapping in the loom). The pores or holes created by a screen using very small wire approaches the diameter of the wire and the open area of the screen for small holes is less than 50%. However, screens offer low back pressure compared to frits since screens are planar in construction and frits derive their functionality from thickness.

Neither the frit nor the screen offers an ideal structure for the containment of a packing or for providing a particle filter in applications that require small hole or pore sizes, particularly for a packed capillary column as used in either liquid chromatography (LC) or capillary electrophoresis (CE). The frit, because of the convoluted route of the pore including paths that contain lateral translations, has high back pressure. While a screen has low back pressure, the screen has a lower limit on "pore" size.

It is an object of this invention to provide a containment structure that reduces the pack pressure relative to a frit structure while not limiting the minimum size of the micropassages to those associated with a screen.

It is a broader object of this invention to provide a microporous structure having low pressure drop and pore diameters of 5 $\mu$m or less.

SUMMARY OF THE INVENTION

This invention accomplishes these objectives with a microporous structure that defines a plurality of singular micro-passages that extend along the axial length of the structure. The plurality of singular micro-passages provide low restriction flow paths for the fluid through the structure. Each singular micro-passage can provide a direct flow path through the structure with a length that equals that of the structure and is free of obstructions The walls that define the micro-passages have a relatively straight configuration that permits extension of wall length without limiting the minimum diameter of the walls or disproportionately increasing pressure through the passages. Increasing the wall length increases the overall strength of the structure to pressure imposed by the fluid or packing.

The structure achieves tight dimensionality of the micro-passages which contributes to the dramatic reduction in back pressure that has been achieved. This dramatic reduction in back pressure is achieved even though the thickness of the structure may exceed that of a conventional compressed particle frit.

The structure is readily manufactured using a modified form of the technique common to glass drawing. The method involves the fabrication of a number of tubes in "macro" to provide a preform which is then drawn down into an extended length of the structure. Lateral slicing of the extended structure supplies wafers of the structure in desired lengths for particular applications. The technology employed to fabricate the structure is similar to the drawing of polyimide coated fused silica or optical waveguide fibers but with distinctly different drawing conditions. A key difference is the use of a low temperature in the drawing furnace compared to either capillary tube drawing or optical waveguide drawing. In drawing the structure of this invention, the furnace is heated to a temperature that is just sufficient to draw the preform. The viscosity of the preform is kept high, near the low end of the softening temperature of the glass, resulting in a tractive force being required to draw the filament from the preform. This is counter to the typical process of drawing optical waveguide where the preform will "drop" due to gravity alone.

The advantage of the formed structure is very high porosity (open space to structure), very low back pressure because the "pore" path is straight with no obstructions and statistically the "pore" diameter falls within a very narrow range. Furthermore, there is no lower range on "pore" diameter. Theoretically, the "pore" diameter can approach the size of the molecules that make up the glass. For example, if fused silica were employed, the "pore" diameter could approach a few nanometers. Overall, this manufacturing process is suitable for manufacturing structures with multiple micro-pores, also referred to as multicapillaries that can have outer diameters of from several millimeters to less than 100 μm. Internal bore diameters of the micro-passages provide pores that can range in size from several hundred micrometers to less than 10 nm. The "pore" field, i.e. the area defined by the outer diameter of the micro-passages, can have diameters of several millimeters to less than 10 nm. The number of pores can range from 7 to several thousand and possibly as high as 100,000. This approach has been found to be very flexible—meaning that the outer size can be varied over a large range, the bores can be varied over an even larger range, and the number of bores within a structure does not seem to have an upper limit.

The preform assembly is typically in the form of a tube that defines the outer circular wall and that retains the internal micro-passage area of the pore field. In most applications, it is preferred that the regularly recurring shape of the capillary cross-section also define capillaries of the same size. The regularly recurring shape of the capillary cross-sections is typically round but may take on oval and rectilinear shapes as well.

A useful feature of this invention is the provision of the internal micro-passages having a regularly recurring shape. The internal open area defined by regular micro-passages, those with cross-sections in the form of the same regularly recurring shape, will equal at least 80% and more preferably at least 90% of the total internal open area in the pore field. Any remaining flow area through the structure is typically in the form of irregular micro-passages having individual cross-sectional areas that are less than the individual cross-sectional areas of the regular micro-passages The relatively small diameter of the irregular micro-passages minimizes the detrimental effect that the presence of the irregular capillaries may have on the different applications for the structure of this invention. The preferred structure of this invention provides uniform micro-passages that virtually eliminate the presence of irregular micro-passages. In this preferred structure, the internal open area defined by regular micro-passages will equal at least 95% and more preferably at least 99% of the total internal open area of the pore field.

This consistency in the manufacturing process yields a substitute for conventional frits and packings wherein each microporous structure from a particular draw is characteristically identical to the other structures. In addition, aside from reducing and simplifying capillary preparation, the ease of assembly for the end user further promotes the repeatability of multiple analyses. Together, the form and employment of the microporous structure ensures the results of each analysis are not influenced by the containment device or the individual's unique method of capillary preparation.

Certain criteria have been found to be useful in producing the micro-passages of this invention. First the inner tubes in the preform generally have a minimum wall thickness below which the inner tubes will distort, which in the completed draw is a wall thickness to hole diameter of at least 1:5. Furthermore, all of the inner tubes should be very consistent in bore and wall thickness or else distortion will occur in the shape of the finished hole and/or the pattern of the holes will be distorted. Moreover, the wall of the outer tube should have sufficient thickness to provide the necessary surface tension for the assembly to collapse or "draw" together during the forming process. The required minimum thickness seems to be dependent on the size of the structure with thicker outer tubing walls generally providing better structures. Another useful parameter when seeking to minimize irregular channel formation is temperature uniformity during the drawing process. It has been found that the drawing apparatus should not permit substantial temperature variations during the drawing operation. Temperature variations should be held to less than 5° C. over the length of the draw.

In some cases, the occurrence of irregular micro-passages may be reduced by packing conduits with a thicker wall section toward the outside of the preform assembly. Wall thickness of the conduits may be increased incrementally with increasing distance from the center of the tube. However, in some assembly draws, particularly as the number of packed conduits increases, minimum irregular micro-passages were produced by uniformly increasing the wall thickness of all of the conduits in one or two of the outermost rows. The wall thickness selection of the conduits to minimize irregular passage formation will vary with size and number of the desired micro-passages as well as the material of the assembly. The additional conduit wall thickness is preferably maintained by decreasing the inside diameter of the conduits. Surprisingly, it has been observed that the conduits with increased wall thickness tend to produce slightly larger passages than the passages produced by conduits with relatively thinner walls.

In addition, when the structure will contain a small number of pores, typically less than 200 micro-passages, and the structure is formed from circular tubes, it is advantageous to arrange the smaller individual tubes of the preform to satisfy certain requirements when placed within a larger tube that supplies the outer wall of the structure. In such arrangements, the multiple tube assembly of the preform should be symmetrical and the total number of tubes should approximate the maximum number of smaller uniform circles that should fit within a larger outer circle. This relationship has been found to provide the most effective packing arrangement. Jacques Dutka, in Machinery Journal, October 1956, gives the maximum number of small circles that may be packed into a larger circle for a number of different packing arrangements Based on these formulas, it has been found that for this invention the typical number of total passageways in a given number of passageway rings is best given by the formula for maximizing circles as presented in the foregoing reference. Therefore, where the desired arrangement for round conduits is as an assembly of rings about a central tube, the number of conduits in the assembly is determined by:

$$N=3n^2+3n+1;$$

where,

N=the total number conduits, and n=the number of rings of conduits around the central conduit.

Where all of the inner conduits have the same outer diameter, the preferred inner diameter of the outer tube is calculated in terms of a "K" factor defined by the above reference. Accordingly, the outer tube has an inner diameter "D" determined by the outer diameter "d" of the inner conduits where:

$D = K*d$

The factor K varies mathematically with the number of inner conduits. Values for K are set forth in the above reference. Examples of specific "K" values are set forth in Table 1 for arrangements that wrap rings of conduits around a central conduit.

TABLE 1

| # of Inner Conduits | I.D. of Outer Tube | # of Inner Conduits | I.D. of Outer Tube |
|---|---|---|---|
| 2–7 | 3 | 122–127 | 13 |
| 8–13 | 4.465 | 128–139 | 13.166 |
| 14–19 | 5 | 140–151 | 13.490 |
| 20–31 | 6.292 | 152–163 | 14.115 |
| 32–37 | 7.001 | 164–169 | 14.857 |
| 38–43 | 7.929 | 170–187 | 15 |
| 44–55 | 8.212 | 188–199 | 15.423 |
| 56–61 | 9.001 | 200–211 | 16.100 |
| 62–73 | 9.718 | 212–223 | 16.621 |
| 74–85 | 10.166 | 224–235 | 16.875 |
| 86–91 | 11 | 236–241 | 17 |
| 92–97 | 11.393 | 242–253 | 17.371 |
| 98–109 | 11.584 | 254–262 | 18.089 |
| 110–121 | 12.136 | | |

When the number of pore forming tubes exceeds several hundred, meeting the approximation of circles within circles does not seem to make any difference However, it is still useful to maintain a relatively tight packing of the smaller tubes within the outer tube. Furthermore, it has been specifically found that minimizing the inner diameter of the outer containment tube for the number of pore forming conduits contained therein dramatically increases the volume of regular capillaries formed during the drawing process.

The structure may be formed from any ductile material that is suitable for drawing when softened to a plastic state. The only apparent restraint suitable material is that the material needs to have drawing properties which afford a reasonably high viscosity at its softening point. Thus, both inorganic glasses and many plastics would be suitable and possibly some metals if they meet the viscosity criteria.

Prior to drawing, the conduits in the tube and conduit preform will preferably have a diameter in a range of from 0.3 to 3 mm and a wall thickness of from 100 $\mu$m to 1 mm. The thickness of the outer tube will usually average from 1 to 5 mm.

Ductile glass materials have been found to be most suitable for production of the structure by the known methods of fabrication. Suitable glass material include lead silicate, borosilicate, conventional glasses (soda lime silicate), and other forms of high purity silica such as quartz or fused silica. A particularly preferred glass material is an alumino-silicate. Glass drawn containment structures of this invention may be an order of magnitude thicker than its metal or polymer compressed frit equivalent and still have lower back pressure. It should also be noted that these glass drawn structures when used as frits have exceptional retaining power for packed capillaries because of their length combined with the high compressive loading glass can tolerate.

Accordingly, in a broad embodiment, this invention is a microporous structure defined by a plurality of singular channels. The structure comprises an axially extended outer wall surrounding an open area. The open area extends continuously over the length of the outer wall between opposite faces of the structure that are bordered by the ends of the outer wall. The faces are transverse or substantially transverse to the axis about which the outer wall extends. The outer wall surrounds a plurality of singular micro-passages that have a maximum diameter not greater than 25 $\mu$m with a maximum diameter of 5 $\mu$m being preferred and a maximum diameter of 2 $\mu$m being particularly preferred. Inner walls of the structure define the micro-passages. The inner walls extend continuously between the opposite faces of the outer wall to define at least a portion of the open area and to substantially inhibit fluid communication between the micro-passages. Typically, the inner walls will have a thickness that is less than half of the thickness of the outer wall.

In another embodiment, this invention is a method of forming a microporous structure. The microporous structure is of the type that includes an axially extended outer wall surrounding a plurality of singular micro-passages that are defined by internal walls and that extend along the axial length of the outer wall. The method inserts a plurality of conduits into a surrounding tube to form a tube and conduit assembly wherein the conduits have relatively small internal and external diameters relative to the tube. Sealing the common openings of the conduits about one end of the tube and conduit assembly forms a drawing preform having a closed end about which all conduits are sealed from fluid flow and an opposite open end about which all conduits are open for fluid flow. The method requires heating of the drawing preform to a softening temperature that permits plastic flow of the drawing stock under an axial traction force but inhibits plastic flow of the drawing stock under its own weight. Simultaneous drawing of the preform by application of the axial tractor force while maintaining the preform at the softening temperature and restricting fluid flow from the open end reduces the interiors of the conduits to a micro-passage size while preventing collapsing closure of the conduit interiors. Collection of a microporous structure from the drawn drawing stock provides a structure that has a plurality of singular micro-passages defined by internal walls and substantially equal in number to the number of conduits.

DESCRIPTION OF THE PREFERRED EMBODIMENTS

Figure 1:
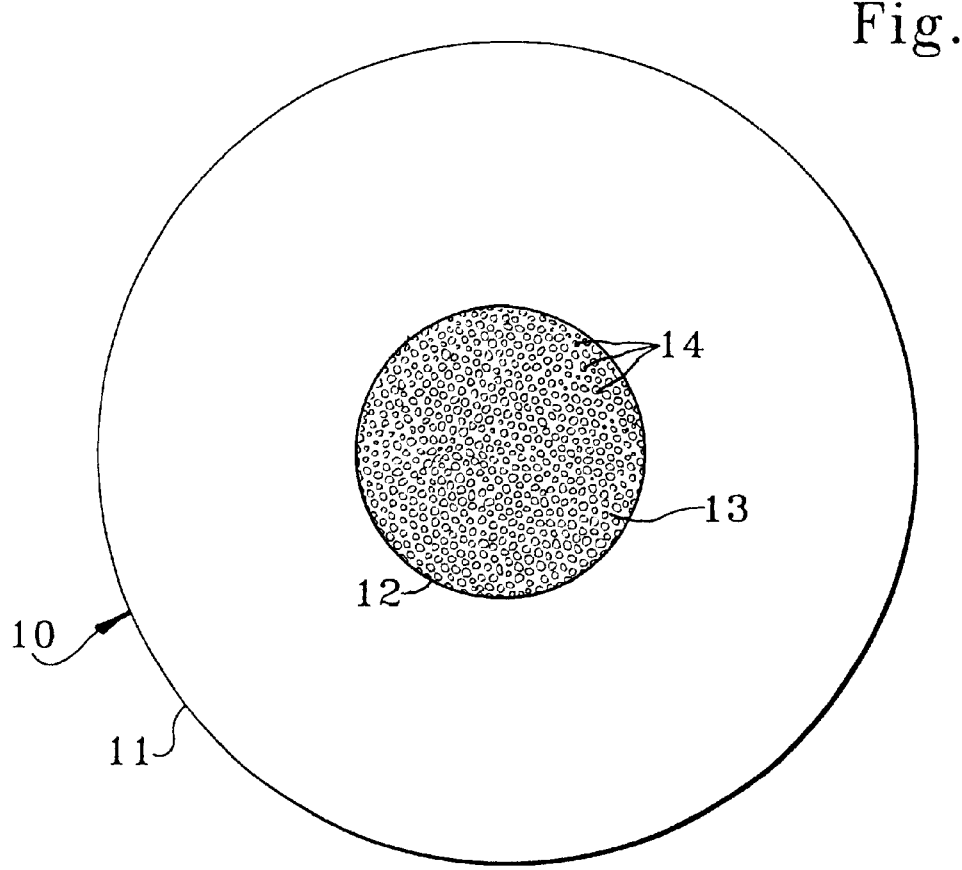
FIG. 1 is a schematic representation of a scanning electron microscope image taken across a transverse section of the microporous structure of this invention.

FIG. 1 shows a cross-section of a typical microporous structure of this invention as recorded by a scanning electron microscope. The schematic represents the structure enlarged by 500 X. The micro-porous structure 10 has an outer wall 11 defining an inner diameter 12 that encircles a plurality of internal walls 13. Internal walls 13 define a plurality of singular microporous passages 14 that provide an open area of a pore field bordered by inner diameter 12. The actual micro-passages have a high degree of uniformity and their total open area equal about 28% of the pore field. A high degree of integral bonding is created between the walls separating the micro-passages.

The structure represented by FIG. 1 contains a total of 599 micro-passages. The structure represented by FIG. 1 was formed using a preform assembled in accordance with packing approach that employs the previously defined equation, $N=3n^2+3n+1$, to fill the circular inside of the large tube with smaller individual circles that initially define the pore forming conduits and to set the inner diameter of the outer tube with the relationship D=K*d. The first several layers formed by the rings of conduits approximate a hex pack configuration but as the layers of rings get larger (n>6) the layers appear to form a circle with some void space As an example of a forming technique for the capillary tubes of this invention, the multi-capillary represented by FIG. 1 was formed by the following method. The outer tube and 217 inner conduits had the following properties.

| outer tube I.D./O.D. | 12.9/15.3 mm |
|---|---|
| inner tube I.D./O.D. | 400/790 $\mu$m |
| glass material | aluminosilicate glass |
| glass melting point | 1120° C. |

The smaller tubes protrude past the outer tube by approximately 25 mm and have their top ends capped to inhibit gas flow in the tubing. This prevents the tubes from collapsing and forming a solid rod during the drawing process. The structure for the drawing stock is assembled one row of conduits at a time using glue or rubber bands to hold each row in place. The assembly is mounted in the drawing tower and allowed to slowly equilibrate at the softening temperature of the glass. This begins to establish the surface forces on the initial part of the assembly and corrects for slight packing errors. The tip of the preform is then dropped and a tractor is used to draw the preform structure from the furnace.

The drawing furnace was operated in the following manner:

| top feed rate | 14.7 mm/min |
|---|---|
| bottom feed rate | 8 M/min |
| carrier gas flow (He)30% Ar 70% | 6 L/min |
| furnace temperature | 983° C. |

Capillaries of other sizes may be produced in varying numbers using the formula or a suitable packing arrangement. The finished size of the micro-passages will usually be in a size range of from 0.5 through 5 $\mu$m. The outer wall of the structure can vary in size from 2 mm to 0.1 mm.

While not confirming any particular theory about the manner in which the method forms the tubes, it is believed that during the drawing process of the assembly, surface tension of the outer structure forces the assembly to conform to its least geometric energy state, relying on a symmetrical distribution of surface tensions of both the outer surface of the assembly and the inner surfaces of the bores coupled with bore pressurization to form a uniform pattern of holes with no void space.

Some additional forming techniques and material properties can improve the uniformity and performance of the microporous structure. Drawing the structure from conduits that themselves having very uniform bores and wall enhances the uniformity of the resulting structure. Uniformity of the individual conduits may be enhanced by drawing the starting conduits down in several stages from large conduits. Uniformity of the resulting capillaries also improves as the alignment of the conduits in the drawing stock becomes more parallel.

Figure 2:
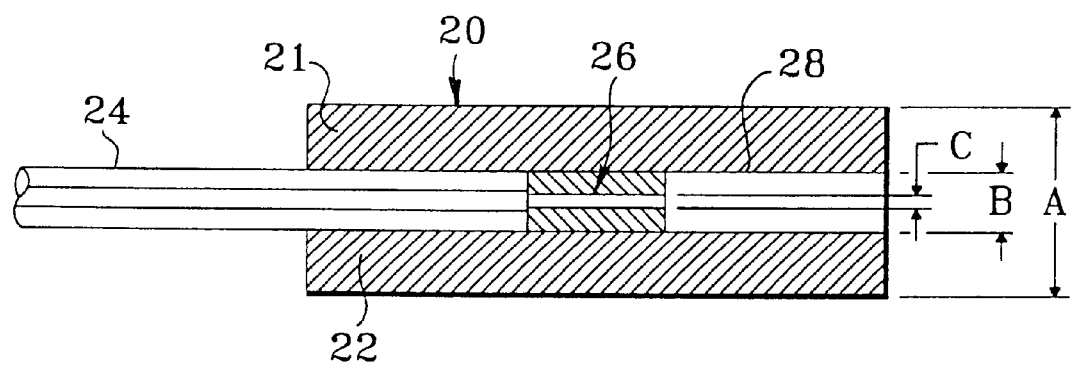
FIG. 2 is a section view of the microporous structure of this invention retained in a sleeve at the end of capillary tube.

The microporous structure of this invention is suited for chromatography applications including the CEC arrangement of the prior art. FIG. 2 shows a typical connection arrangement that uses microporous structure of this invention as a frit. An end 21 of a connector 20 in the form of a fused silica sleeve retains an end 22 of capillary tubing 24 in contact with the microporous structure 26. Typical dimensions for the fused silica sleeve include an outer diameter (A) of 1400 $\mu$m, an inner diameter (B) of 370 $\mu$m, and a length of 3300 $\mu$m. Structure 26 has an outside diameter of 365 $\mu$m, a pore field diameter (C) of 125 $\mu$m that contains 599 micro-passages having an average diameter of 2.9 $\mu$m, and a length of 800 $\mu$m. A suitable detection or assembly may communicate with the outer end of the structure 36 through end 28 of connector 22.

The connection is assembled by placing the structure over the end of the capillary and inserting the capillary into the sleeve with the capillary bottomed out against the microporous structure An appropriate bonding agent such as a UV curing acrylate may be used to retain the capillary and the structure in the sleeve.

In addition to its use as a replacement for frits and screens, the microporous structure of this invention has a variety of applications. Its use as a flow restrictor for regulating the discharge of hazardous fluids presents a simple application for the assembly outside the field of chromatography In terms of broad applications, the micro-passages may serve as mini-conduits for retaining, conveying, or separating fluids.

The structure provided by this also provides unique length-to-diameter properties. The aspect ratio (L/D ratio) for the conduit structure of this invention provides extremely long length relative to the small diameters of the pores or micro-passages. A draw of the structure with a length of only 10 mm can provide 0.5 $\mu$m pores with an aspect ratio of 20,000. The same length draw to obtain 10 nm pores will provide an aspect ratio of over one million. Therefore, the structure of this invention can provide long relative path lengths in a very short device.

What is claimed is:

1. A method of forming a microporous structure comprising an axially extended outer wall that surrounds a plurality of singular micro-passages defined by internal walls and wherein the micro-passages extend along the axial length of the outer wall, the method comprising:

a) inserting a plurality of conduits into a surrounding tube to form a tube and conduit assembly wherein the conduits have relatively small internal and external diameters relative to the tube;

b) sealing the common openings of the conduits about one end of the tube and conduit assembly to form a drawing preform having a closed end about which all conduits are sealed from fluid flow and an opposite open end about which all conduits are open for fluid flow;

c) heating the drawing preform to a softening temperature that permits plastic flow of the drawing stock under an axial traction force but inhibits plastic flow of the drawing stock under its own weight;

d) simultaneously drawing the drawing preform by application of a tractor while maintaining the preform at the softening temperature and restricting fluid flow from the open end to reduce the interiors of the conduits to a micropore size while preventing collapsing closure of the conduit interiors; and, e) collecting a microporous structure from the drawn drawing stock that has a plurality of singular micro-passages defined by internal walls and substantially equal in number to the number of conduits.

2. The method of claim 1 wherein drawing of the preform reduces the diameter at the open end of the preform upstream of the open end of the preform, restricts gas flow out of the interiors of the conduits, and thereby provides the restriction to fluid flow at the open end.

3. The method of claim 1 wherein the tube and conduit assembly comprises a glass material.

4. The method of claim 1 wherein the tube and conduit assembly comprises an alumino-silicate glass.

5. The method of claim 1 wherein the tube and conduits have a round cross-section.

6. The method of claim 5 wherein prior to drawing the tubes in the tube and conduit assembly, the conduits have a diameter in a range of from 0.3 to 3 mm and a wall thickness of from 100 µm to 1 mm.

7. The method of claim 1 wherein the number of conduits in the assembly does not exceed 200 conduits and the conduits are arranged in the assembly as rings about a central conduit and the number of conduits in the assembly is determined by the following formula:

$$N=3n^2+3n+1;$$

where,

N=the total number conduits, and n=the number of rings of conduits around the central conduit.

8. The method of claim 7 wherein the conduits are arranged in the assembly as rings about a central conduit and the number of conduits in the assembly is determined by the following formula:

$$D=K*d$$

where D=the inner diameter of the tube, d=the outer diameter of the conduits, and K=the factor for determining the minimum diameter of a circle that can retain the number of inner conduits in an arrangement with a central conduit.

* * * * *